United States Patent
Vandewalle

[19]

[11] Patent Number: 6,067,701
[45] Date of Patent: *May 30, 2000

[54] METHOD FOR FORMING A WORK HARDENED MODULAR COMPONENT CONNECTOR

[75] Inventor: Mark V. Vandewalle, Pierceton, Ind.

[73] Assignee: Biomet, Inc., Warsaw, Ind.

[ * ] Notice: This patent issued on a continued prosecution application filed under 37 CFR 1.53(d), and is subject to the twenty year patent term provisions of 35 U.S.C. 154(a)(2).

[21] Appl. No.: 08/996,026

[22] Filed: Dec. 22, 1997

Related U.S. Application Data

[63] Continuation-in-part of application No. 08/720,190, Sep. 25, 1996, abandoned.

[51] Int. Cl.[7] .................................................. B23P 13/64
[52] U.S. Cl. ..................... 29/558; 29/DIG. 49; 623/901; 403/334
[58] Field of Search ...................... 29/557, 558, DIG. 49; 623/18, 19, 20, 901; 403/334

[56] References Cited

U.S. PATENT DOCUMENTS

| | | |
|---|---|---|
| 1,784,866 | 12/1930 | Fahrenwald . |
| 1,891,405 | 12/1932 | Ericksson . |
| 2,067,751 | 1/1937 | Beegle . |
| 3,058,386 | 10/1962 | Morrow . |
| 3,126,561 | 3/1964 | Orloff ........................................ 470/11 |
| 3,433,514 | 3/1969 | Feighofen . |
| 3,516,874 | 6/1970 | Maker et al. . |
| 3,610,075 | 10/1971 | Fabish . |
| 3,656,785 | 4/1972 | Lothar . |
| 3,707,865 | 1/1973 | Oriani . |
| 3,776,651 | 12/1973 | Peter et al. . |
| 4,021,084 | 5/1977 | Garner . |
| 4,100,785 | 7/1978 | Bishop . |
| 4,187,559 | 2/1980 | Grell et al. . |
| 4,258,084 | 3/1981 | Hayden, Sr. . |
| 4,286,371 | 9/1981 | Falcioni . |

(List continued on next page.)

FOREIGN PATENT DOCUMENTS

| | | | |
|---|---|---|---|
| 629929 | 10/1961 | Canada ..................................... 269/47 |
| 737145 | 6/1966 | Canada ................................... 403/381 |
| 198 163 | 10/1986 | European Pat. Off. . |
| 640894 | of 0000 | France ..................................... 29/446 |
| 1 045 679 | 3/1955 | France . |
| 1 095 064 | 12/1960 | Germany . |

*Primary Examiner*—David P. Bryant
*Attorney, Agent, or Firm*—Harness, Dickey & Pierce, P.L.C.

[57] ABSTRACT

A method for forming a work hardened modular component connector for use in orthopedic surgery. This method includes machining a member which forms a portion of the orthopedic implant into an initial configuration having an oversized region. Work hardening a portion of the oversized region of the member. Machining the member into a final precision configuration upon work hardening at least a portion of the oversized region of the member.

20 Claims, 5 Drawing Sheets

U.S. PATENT DOCUMENTS

| | | |
|---|---|---|
| 4,305,678 | 12/1981 | Majoor . |
| 4,419,804 | 12/1983 | Axthammer . |
| 4,423,650 | 1/1984 | Decker et al. . |
| 4,606,102 | 8/1986 | Riethmuller . |
| 4,620,803 | 11/1986 | Vezirian . |
| 4,775,426 | 10/1988 | Murley et al. . |
| 4,787,907 | 11/1988 | Carignan . |
| 4,822,366 | 4/1989 | Bolesky . |
| 4,881,763 | 11/1989 | Guido et al. . |
| 4,892,547 | 1/1990 | Brown . |
| 4,917,530 | 4/1990 | Engelhardt et al. . |
| 4,936,853 | 6/1990 | Fabian et al. . |
| 4,944,757 | 7/1990 | Martinez et al. . |
| 5,002,578 | 3/1991 | Luman . |
| 5,018,900 | 5/1991 | Darrin . |
| 5,080,685 | 1/1992 | Bolesky et al. . |
| 5,122,141 | 6/1992 | Simpson et al. . |
| 5,152,796 | 10/1992 | Slamin . |
| 5,169,597 | 12/1992 | Davidson et al. . |
| 5,192,331 | 3/1993 | Spotorno et al. . |
| 5,194,066 | 3/1993 | Van Zile . |
| 5,306,272 | 4/1994 | Cohen et al. . |
| 5,330,535 | 7/1994 | Moser et al. . |
| 5,362,311 | 11/1994 | Amino et al. . |
| 5,397,360 | 3/1995 | Cohen et al. . |
| 5,405,395 | 4/1995 | Coates . |
| 5,413,605 | 5/1995 | Ashby et al. . |
| 5,489,311 | 2/1996 | Cipolletti . |
| 5,501,122 | 3/1996 | Leicht et al. . |
| 5,573,401 | 11/1996 | Davidson et al. . |
| 5,626,889 | 5/1997 | Bittner . |
| 5,645,606 | 7/1997 | Oehy et al. . |

10# METHOD FOR FORMING A WORK HARDENED MODULAR COMPONENT CONNECTOR

CROSS-REFERENCE TO RELATED APPLICATIONS

This application is a continuation-in-part application of U.S. Ser. No. 08/720,190, entitled "MODULAR COMPONENT CONNECTOR", filed Sep. 25, 1996, which is now abandoned.

BACKGROUND OF THE INVENTION

1. Field of the Invention

This invention relates generally to a modular component connector for joining modular components together and, more particularly, to a method for forming a work hardened modular component connecter for coupling together modular components of a knee, hip or shoulder prosthesis for use in orthopedic surgery.

2. Discussion of the Related Art

Various modular prosthetic devices are currently known and utilized during orthopedic surgeries. These modular prosthetic devices include modular knee, hip and shoulder prosthesis. Since the modular prostheses consist of multiple components, various coupling mechanisms are used to secure or couple the modular components together.

One of the primary and most common coupling mechanisms employed consists of a Morse type taper 10, shown in FIG. 1. The Morse type taper 10 is generally known as a "self-holding" or "self-locking" taper because the angle of the conical taper is generally 2° to 4° which creates considerable friction to lock a male portion 12 into a female portion 14.

However, because of tolerance effects during manufacturing of the Morse type taper 10, it is very difficult to manufacture the male portion 12 and the female portion 14, so that the male portion 12 axially engages along the entire female portion 14. Accordingly, in some instances the male portion 12 may only contact the female portion 14 at one contact point at an unknown location within the Morse type taper 10, as shown by reference numeral 16. This single contact point 16 occurs because in some instances the conical angle of the male portion 12 does not mate with the conical angle of the female portion 14. This condition may in turn allow for micro-motion to occur between the components resulting in fretting at the contact point 16. Such fretting may eventually lead to stress fractures along the loaded contact point 16 that could result in catastrophic failure of the connector.

Moreover, should the male portion 12 axially engage along the entire female portion 14, the Morse type taper 10 also poses other difficulties. For example, where the male portion 12 exits or contacts the female portion 14 at reference point 17, there is generally a stress concentration at this exit point 17. This stress concentration point runs about the circumference of the male portion 12 and is one the areas most likely to fail over time due to the stress concentration along this area.

Other taper connections, such as those disclosed in U.S. Pat. No. 4,917,530 to Englehardt et al. are designed to preclude contact between the male tapered member and the peripheral edge defining the mouth of the bore in the female member. However, Englehardt et al. does not address the problem of having only one contact point between the male and female portions at a location that may vary within the bore, thereby permitting micro motion. Rather, Englehardt et al. assumes axial contact, that is, full face to face contact of the adjacent tapered surfaces of the male portion and female bore and is only concerned with impingement at the mouth of the female bore. Therefore, Englehardt et al does not reduce micro motion caused by practical tolerance effects or the potential resulting stress fractures associated therewith. Nor does Englehardt et al. suggest any ways to increase strength at the stress concentration point 17, other than to reduce contact between the male member and the peripheral edge of the female member.

Other connection mechanisms have also utilized ion implantation along the connection members to provide an ion layer in these areas. However, ion implantation does not appear to provide any appreciable increase in strength because the surface thickness of the implanted ion layer is only generally a few microns thick. Alternatively, mechanical hardening techniques have not even been considered, nor utilized because of the tight tolerance effects of such connections and the inability to perform such mechanical hardening with such tight tolerance effects.

What is needed then is a modular component connector for a modular knee, hip or shoulder prosthesis or any other type prosthesis which does not suffer from the above-mentioned disadvantages. This in turn, will provide a modular component connector that substantially reduces or eliminates micro-motion, reduces the possibility of stress fractures, provides positive contact along at least two predictably located separated contact points for increased stability, provides a mechanically hardened surface at least along one contact point or stress concentration region to provide a thick surface hardening and a stronger connection, and provides a cost effective and easily manufacturable modular component connector. It is, therefore, an object of the present invention to provide a method for forming a work hardened modular component connector for use with modular prosthetic devices.

SUMMARY OF THE INVENTION

In accordance with the teachings of the present invention, a method for forming a work hardened modular component connector for use in orthopedic surgery is disclosed. The work hardened modular component connector provides a connection between modular components of orthopedic implants with improved load or sheer strengths. This is basically achieved by work hardening at least a portion of the modular component connector.

In one preferred embodiment, a method for forming a work hardened modular component connector for use in orthopedic surgery is set forth. This method includes the steps of, machining a member which forms a portion of an orthopedic implant into an initial configuration having an oversized region, work hardening at least a portion of the oversized region of the member, and machining the member into a final precision configuration.

Use of the present invention provides a method for forming a work hardened modular component connector for joining modular components together. As a result, the aforementioned disadvantages associated with the currently available methods and techniques for joining modular components together have been substantially reduced or eliminated.

BRIEF DESCRIPTION OF THE DRAWINGS

Still other advantages of the present invention will become apparent to those skilled in the art after reading the following specification and by reference to the drawings in which:

FIGS. 8A–10 illustrate a method for forming the work hardened modular component connector according to the teachings of the third preferred embodiment of the present invention.

DETAILED DESCRIPTION OF THE PREFERRED EMBODIMENT(S)

The following description of the preferred embodiments concerning a modular component connector for coupling modular components of a knee, hip or shoulder prosthesis or any other type prosthesis for use in orthopedic surgery are merely exemplary in nature and are in no way intended to limit the invention or its application or uses. Moreover, while the present invention is described in detail below with reference to coupling modular components of a knee, hip or shoulder prosthesis for use in orthopedic surgery, it will be appreciated by those skilled in the art that the present invention is clearly not limited to only these types of prosthetic devices for orthopedic surgery and may be utilized with various other orthopedic implants, as well as with any other type of device requiring connection of various modular components.

Figure 1:
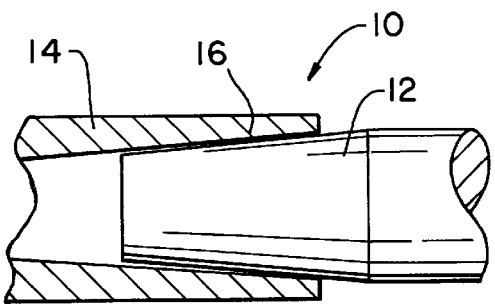
FIG. 1 is a cross-sectional view of a prior art Morse type taper.
Figure 2:
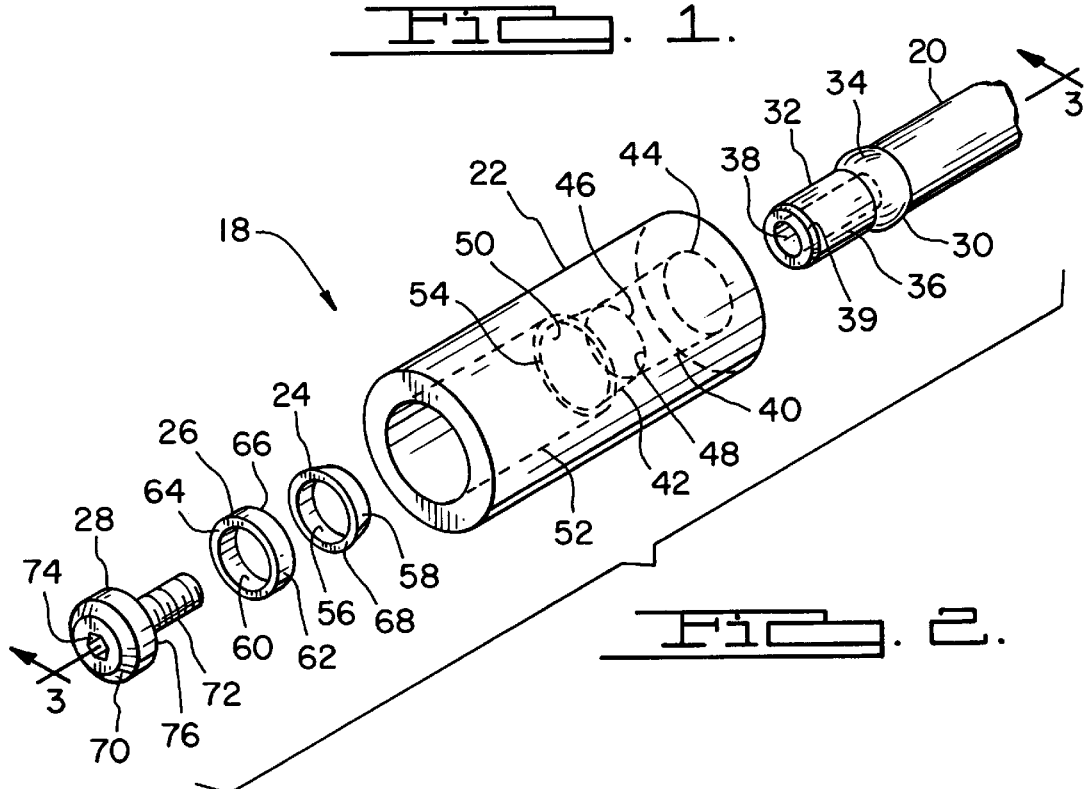
FIG. 2 is an exploded perspective view of a work hardened modular component connector according to the teachings of a first preferred embodiment of the present invention.
Figure 3:
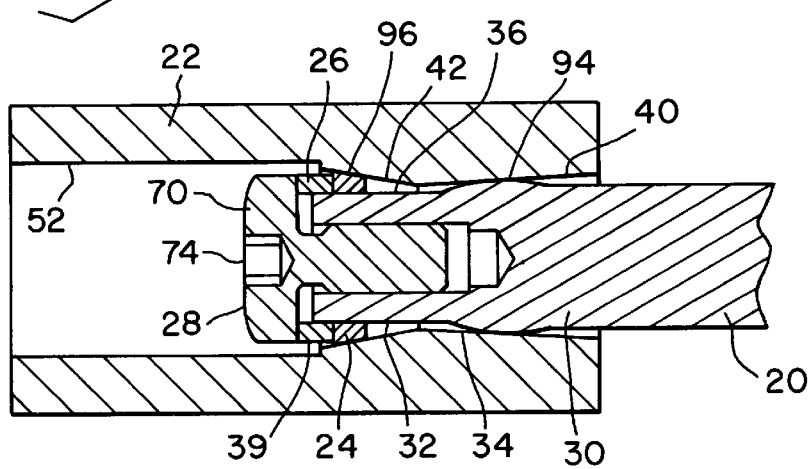
FIG. 3 is an assembled cross-sectional view of the work hardened modular component connector shown in FIG. 2 taken along line 3—3 of FIG. 2.

Referring to FIGS. 2–3, a work hardened modular component connector 18 according to the teachings of a first preferred embodiment of the present invention is shown. The work hardened modular component connector 18 includes a male member 20, a female member 22, a ferrule 24, a thrust washer 26 and a bolt 28. The components of the work hardened modular component connector 18 are preferably made from suitable biocompatible material such as titanium, stainless steel, titanium alloys, cobalt-chrome-molybedenum alloys etc.

The male member 20, which includes the ferrule 24, is preferably made from titanium and includes a first elongated portion 30 and a second elongated portion 32. The first elongated portion 30 has a toroidal or bulbous external surface 34 having a radial engagement or contact surface. The radial external surface 34 is mechanically or work hardened by cold working, further described herein, which increases the load strength of the final construction by as much as 25%. The second elongated portion 32 is concentric with and axially extends from the first elongated portion 30. The second elongated portion 32 includes an external cylindrical surface 36 having a radial engagement or contact surface and a threaded internal bore 38. Located at the end of the second elongated portion 32 and concentric therewith is a lead-in step or notch 39.

The female member 22 is preferably made from titanium and defines an elongated bore having a first elongated frustoconical bore 40 adjacent and concentric with a second elongated reverse frustoconical bore 42. The first elongated bore 40 includes an entrance opening 44 tapering to a smaller exit opening 46 at an angle of about four (4°) degrees inclusive or about two (2°) degrees per side. The second elongated bore 42 has an entrance opening 48 coupled to the exit opening 46. The entrance opening 48 tapers to a larger exit opening 50 at an angle of about twenty (20°) degrees inclusive or about ten (10°) degrees per side. The taper in the first elongated bore 40 is opposite or reverse of the taper in the second elongated bore 42. Concentric with the first elongated bore 40 and the second elongated bore 42 is a third elongated cylindrical bore 52 forming a ledge 54 at the exit opening 50 which is an access port for the bolt 28.

The ferrule 24 preferably consists of a soft commercially pure titanium alloy annular member having an internal cylindrical sidewall 56 and an external conical sidewall 58. The internal cylindrical sidewall 56 is formed to slidably and radially engage the external cylindrical surface 36 of the male member 20, while the external conical sidewall 58 having a radial engagement or contact surface is formed to slidably and radially engage the second elongated frustoconical bore 42 of the female member 22. The ferrule 24 is a deformable annular member which is operable to deform upon the internal cylindrical sidewall 56 and the external conical sidewall 58 slidably engaging the male member 20 and the female member 22, further discussed herein.

The thrust washer 26 is preferably made of cobalt-chrome-molybedenum and includes an internal cylindrical sidewall 60, an external cylindrical sidewall 62, a first annular surface 64 and a second annular surface 66. The internal cylindrical sidewall 60 slidably engages the external cylindrical surface 36 of the male member 20, while the second annular surface 66 engages an annular surface 68 of the ferrule 24. The external cylindrical sidewall 62 is of a diameter sufficient to allow the ferrule 24 to deformably engage the male member 20 and the female member 22 as the ferrule 24 is slidably engaged along the external cylindrical surface 36.

The bolt 28 is preferably made of titanium and includes a head 70 and a threaded shaft 72 that threadably engages the threaded bore 38 in the male member 20. The head 70 includes a hex drive 74 or other suitable drive. The head 70 includes a circular planar underside 76 which engages the first annular surface 64 of the thrust washer 26.

Figure 4A:
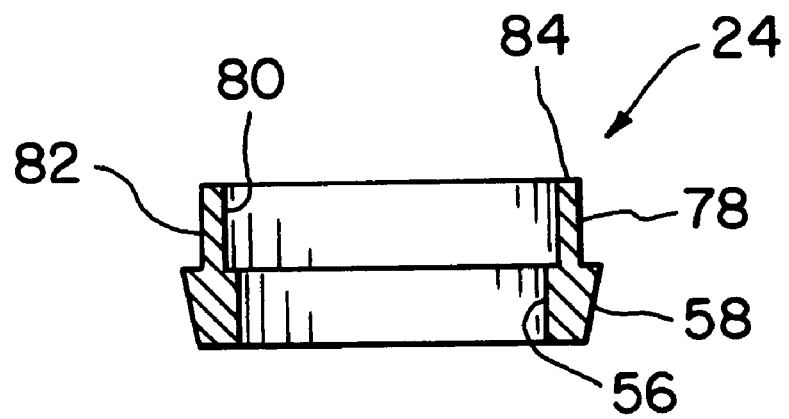
FIG. 4A is a cross-sectional view of a ferrule according to the teachings of a second preferred embodiment of the present invention.

Turning to FIG. 4A, a second preferred embodiment of the ferrule 24' is shown. In this regard, like reference numerals will be used to identify similar structures as described with respect to the first preferred embodiment of the ferrule 24. The ferrule 24', shown in FIG. 4A, is to be used in place of utilizing a thrust washer 26. The ferrule 24' includes the internal cylindrical sidewall 56' and the external conical sidewall 58' as with the first preferred embodiment. The ferrule 24' of the second preferred embodiment also includes an annular collar 78 used in place of the thrust washer 26 having an internal cylindrical sidewall 80 and an external cylindrical sidewall 82, each being concentric with the internal cylindrical sidewall 56'. The collar 78 also includes an annular surface 84 which is operable to be engaged by the underside 76 of the head 70. By providing an internal cylindrical sidewall 80 having a diameter larger than the internal cylindrical sidewall 56' and an external cylindrical sidewall 82 having a diameter smaller than the largest diameter portion of the external conical sidewall 58', the collar 78 will not bind upon deformably radially engaging the ferrule 24' with the male member 20 and the female member 22.

Figure 4B:
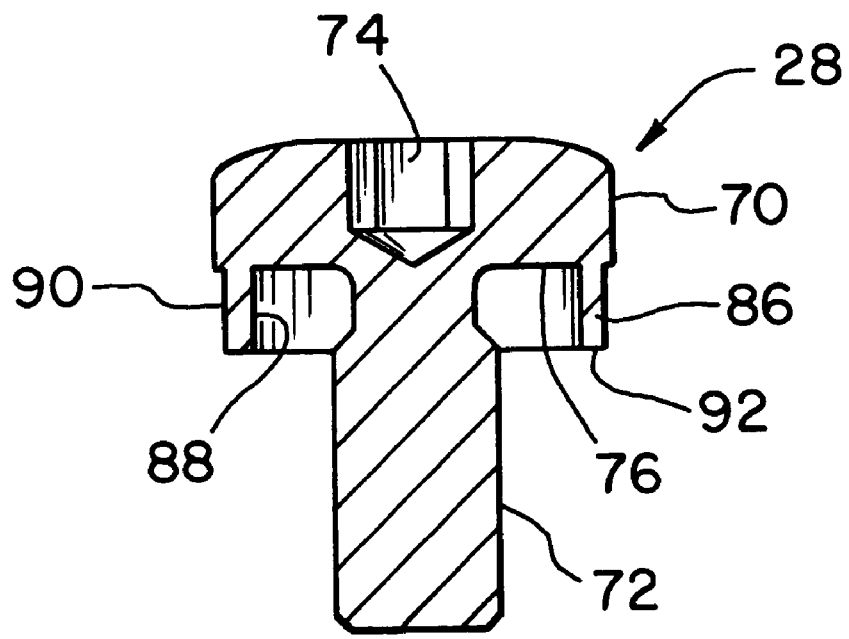
FIG. 4B is a cross-sectional view of a bolt according to the teachings of a second preferred embodiment of the present invention.

Turning to FIG. 4B, a second preferred embodiment of the bolt 28' is shown. In this regard, like reference numerals will be used to identify similar structures as described with respect to the first preferred embodiment of the bolt 28. Here again, the bolt 28', as shown in FIG. 4B, is configured to be utilized in place of using a thrust washer 26. The bolt 28' includes the head 70', the threaded shaft 72' and the hex drive 74'. Positioned at the underside 76' of the head 70', is an annular collar 86. The annular collar 86, has an internal cylindrical sidewall 88 and an external cylindrical sidewall 90 forming an annular surface 92 therebetween. The internal cylindrical slidewall 88 is of a larger diameter than the external cylindrical surface 36, while the diameter of the external cylindrical slidewall 90 is smaller than the largest diameter portion of the external conical sidewall 58. This enables the annular surface 92 to engage the annular surface 68 of the ferrule 24 without binding on the male member 20 or the female member 22. It should also be noted that the thrust washer 26 may simply be eliminated by using an appropriately sized ferrule 24 and the first preferred embodiment of the bolt 28.

Referring back to FIG. 3, the operation of assembling the work hardened modular component connector 18 will now be described. First, it is to be understood that the work hardened modular component connector 18 may be utilized with various modular orthopedic implants such as knee, hip or shoulder prosthesis, as well as with any other device having modular components which require joining or coupling of the modular components. For example, the male member 20 may form a part of a stem for a modular hip prosthesis, while the female member 22 may form the proximal portion of the modular hip prosthesis. The male member 20 is first inserted into the female member 22 such that the first elongated portion 30 just radially engages the first elongated bore 40 at the mechanically or work hardened toroidal or bulbous external surface 34. This radial engagement creates a first positive contact point 94 at a substantially predetermined known location situated at one end of the modular component connector 18.

The ferrule 24 is then passed through the cylindrical third bore 52 and over the notch 39 until the internal cylindrical sidewall 56 slidably engages the external cylindrical surface 36. As the internal cylindrical sidewall 56 engages the external cylindrical surface 36, the external conical sidewall 58 slidably and radially engages the second elongated frustoconical bore 42 of the female member 22. The thrust washer 26 is then passed through the cylindrical third bore 52 and positioned atop the ferrule 24 such that the second annular surface 66 of the thrust washer 26 engages the annular surface 68 of the ferrule 24. The bolt 28 is finally passed through the cylindrical third bore 52 with the shaft 72 being threadably received within the threaded bore 38 of the male member 20.

The male member 20 may then be struck to fully seat the male member 20 within the female member 22. Upon tightening the bolt 28, the underside 76 of the head 70 forces the thrust washer 26 into engagement with the ferrule 24, while the ferrule 24 deformably engages about the external cylindrical surface 36 and radially within the elongated frustoconical bore 42. This simultaneously provides the first positive contact point 94 at a first position and a second positive contact point 96 at a second position. The first positive contact point 94 establishes a substantially annular or radial contact surface substantially 360° around the mechanically or work hardened bulbous surface 34 between the bulbous surface 34 and the first elongated bore 40. The second positive contact point 96 establishes a substantially annular or radial contact surface substantially 360° around where the ferrule 24 deformably engages both the cylindrical surface 36 of the male member 20 and the second elongated frustoconical bore 42 of the female member 22.

The spaced apart or displaced first positive contact point 94 with the second positive contact point 96, positioned substantially at each end of the work hardened modular component connector 18, provides a substantially stable and strong connector 18 which substantially reduces or eliminates any micro motion. Moreover, the primary load bearing site or the first positive contact point 94 includes the mechanically or work hardened bulbous contact surface 34 that substantially increases the load strength along this contact point 94 by as much as 25%. Still further, it should be noted that the male member 20 does not contact or engage the female member 22 between the spaced apart first and second positive contact points 94 and 96 or before the first positive contact point 94, thereby eliminating any regions that would be prone to fretting and subsequent stress fractures.

The method of forming the work hardened modular component connector 18 will now be described with reference to FIGS. 3 and 5A–5C. The female member 22 is formed by machining or boring out the first elongated bore 40, the second elongated bore 42, and the third elongated bore 52 using an appropriate tool such as a CNC boring machine. Once the female member 22 is formed, the first step in forming the male member 20 is to provide a cylindrical titanium piece of stock. This piece of stock is inserted into a conventional precision CNC lathe. Once positioned within the lathe, the first elongated portion 30 and the second elongated portion 32 are formed to an initial configuration by machining or axially turning the cylindrical piece of stock and axially drawing a single point cutting member along the stock. The external cylindrical surface 36 is formed slightly oversized and the toroidal bulbous surface 34 is initially formed with a protruding semi-spherical or bulbous hump 98 formed with a radius which varies to yield a radially displaced thickness of between about 0.002 inches to about 0.006 inches and an axial width of about 0.200 inches centered about the first positive contact point 94. The external cylindrical surface 36 and the bulbous external surface 34 having the protruding hump 98 is formed during the same machining or cutting process so that the surfaces 34 and 36 are substantially concentric with one another.

Figure 5A:
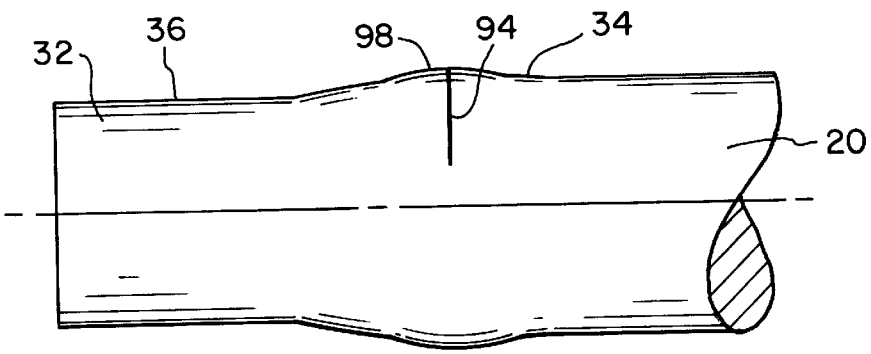
FIGS. 5A–5C illustrate a method for forming a work hardened modular component connector according to the teachings of the first preferred embodiment of the present invention.

Once the male member 20 has been shaped to its initial configuration as shown in FIG. 5A, the bulbous or toroidal external surface 34 is mechanically surface or work hardened by cold-working. Specifically, the protruding hump 98 is rolled with two rollers or knurling wheels 100 having a radius of about 3.5 inches at the first positive contact point 94. This rolling or cold-working with the rollers 100 mechanically or work hardens and shapes the bulbous surface 34 to a sufficient hardened thickness which thereby increases the load strength along the first positive contact point 94 by as much as 25% over a non-mechanically hardened surface. Those skilled in the art would also understand that various other mechanical hardening techniques could also be performed at the bulbous surface 34, such as by shot peening or precision impacting along this area. Mechanical or work hardening has been found to be particularly successful here because of the thick surface hardening created at the bulbous surface 34.

Figure 5B:
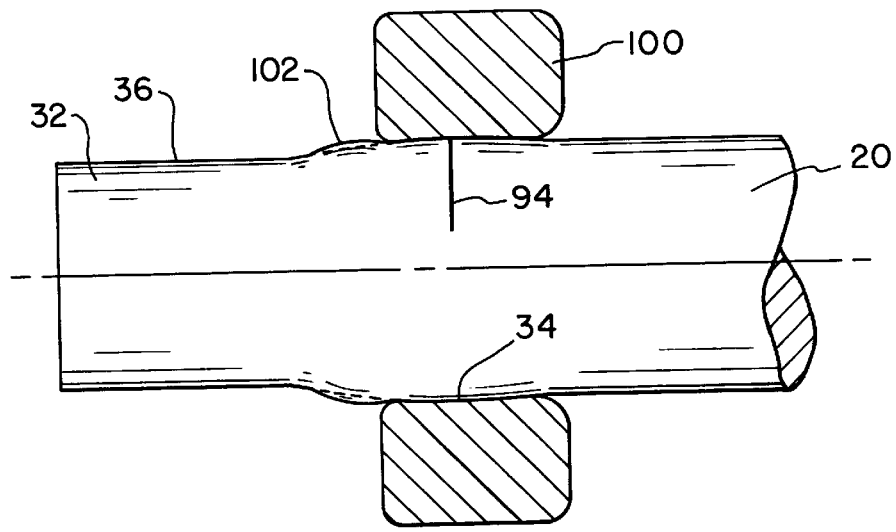
Figure 5C:
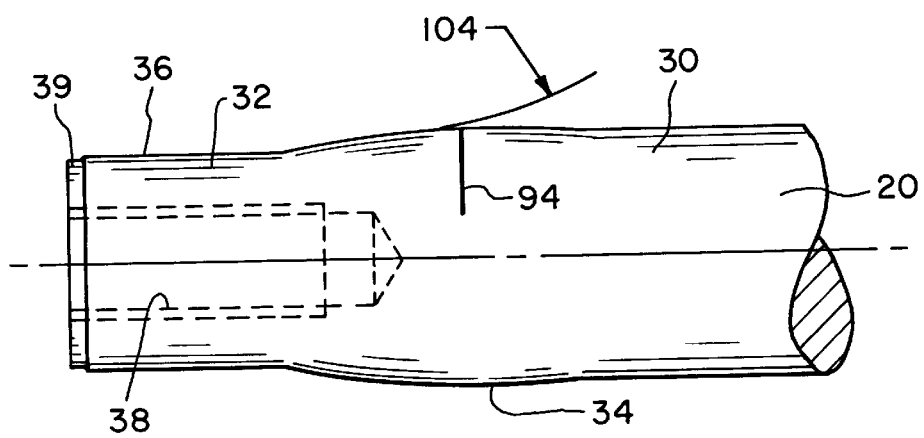

The cold-working performed by the rollers 100 displaces excess material 102 from the protruding hump 98 adjacent to the rollers 100 and can distort the external cylindrical surface 36, as shown in FIG. 5B. To remove the excess material 102, the male member 20 is machined or turned again on the precision lathe, thereby removing the excess material 102 and reducing the oversized external cylindrical surface 36 to its proper size or final precision configuration, as well as forming the notch 39 into the end of the external cylindrical surface 36. The displaced material 102 is removed by the lathe following the path 104, shown in FIG. 5C, which sufficiently removes the excess material 102, but does not remove the mechanically or work hardened surface 34 which will be centrally positioned about the first positive contact point 94. The threaded bore 38 is finally formed within the end of the male member 20.

Figure 6:
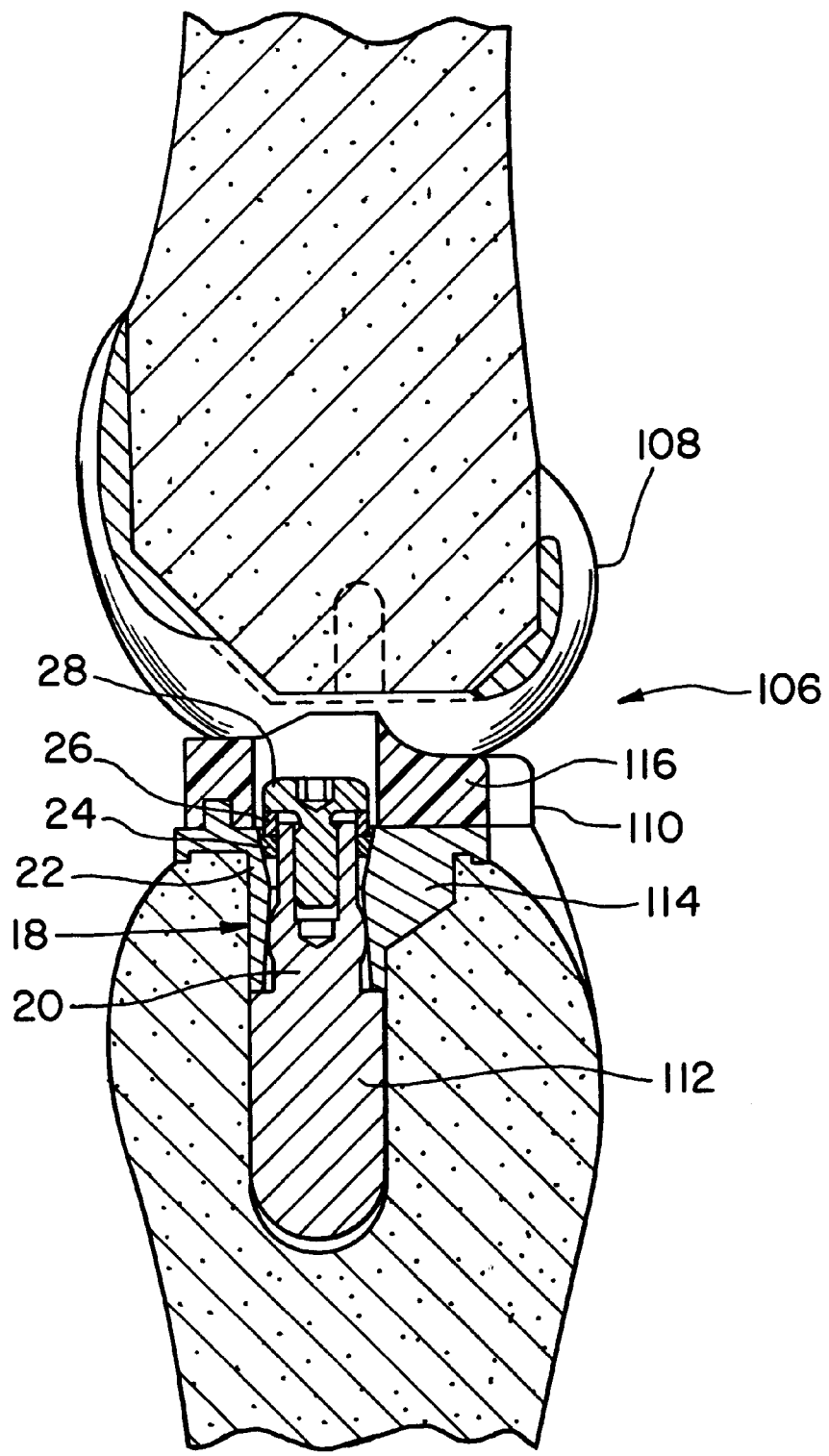
FIG. 6 is a cross-sectional view of a modular knee prosthesis which incorporates the work hardened modular component connector according to the teachings of the first preferred embodiment of the present invention.

Turning to FIG. 6, the work hardened modular component connector 18 is shown incorporated into a modular knee prosthesis 106. The modular knee prosthesis 106 includes a femoral component 108 and tibial component 110. The tibial component 110 incorporates the male member 20 into an extension 112 and the female member 22 into a tibial base 114. Positioned atop the tibial base 114 is a tibial insert 116.

During orthopedic surgery, the extension 112 having the appropriate length is selected which includes the male member 20. Once selected, the extension 112 is engaged with the tibial base 114 housing the female member 22. The ferrule 24 is then slidably engaged on the external cylindrical surface 36 between the male member 20 and the female member 22, with the thrust washer 26 engagably positioned atop the ferrule 24. The tibial insert 116 is positioned atop the tibial base 114, and the bolt 28 is passed therethrough and is threadably engaged within the threaded bore 38 to secure the three modular components. Use of the work hardened modular component connector 18 can also be incorporated into hip, shoulder or various other orthopedic implants for use during orthopedic surgery or with any other device which requires coupling of modular components.

Figure 7:
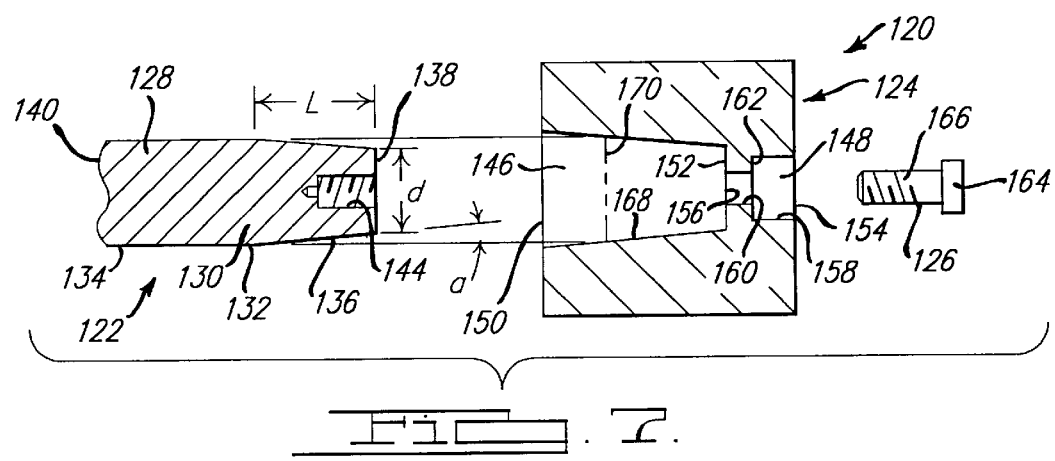
FIG. 7 is an exploded cross-sectional view of a work hardened modular component connector according to the teachings of a third preferred embodiment of the present invention.

Turning now to FIG. 7, a work hardened modular component connector 120 according to the teachings of a third preferred embodiment of the present invention is shown in cross section. The work hardened modular component connector 120 includes a male member 122, a female member 124, and an assembly bolt 126. Here again, the components of the work hardened modular component connector 120 are preferably made from suitable bio-compatible material such as titanium, stainless steel, titanium alloys, cobalt-chrome-molybedenum alloys etc.

The male member 122 is preferably made from titanium and includes a first cylindrical portion 128 and a second conically tapered portion 130 having a transition corner 132 located there between. The first cylindrical portion 128 has an external machined cylindrical surface 134 and the second conically tapered portion 130 has an external machined tapered surface 136. The transition corner 132 is formed as a slightly rounded corner where the tapered portion 130 transitions to the cylindrical portion 128. The transition corner 132 is mechanically or work hardened by cold working, further discussed herein to substantially increase the load or sheer strength in this stress concentration area.

The male member 122 further includes a first proximal end 138 and a second distal end 140. Generally, the length "L" of the second tapered portion 130 between the transition corner 132 and the first proximal end 138 will range between about 5 mm to 50 mm. The cylindrical diameter "d" of the first proximal end 138 will generally range between about 5 mm to 30 mm. The angle "a" of the tapered portion 130 will generally range between about 0.5° to 5.0° per side or 1.0° to 10.0° inclusive. The first proximal end 138 also defines a threaded internal bore 144 which is operable to threadably receive the assembly bolt 126.

The female member 120 is also preferably made from titanium and defines an elongated bore passing there through having a first elongated frustoconical bore 146 adjacent and concentric with a second elongated cylindrical bore 148 that is operable to receive the assembly bolt 126. The first frustoconical bore 146 includes an entrance opening 150 tapering to a terminal or exit opening 152 at an angle substantially congruent with the tapered portion 130 of the male member 122. The second elongated bore 148 also includes an entrance opening 154 and an exit opening 156. The second elongated bore 148 is defined by a first cylindrical bore 158 and a second cylindrical bore 160 with an annular shoulder 162 positioned therebetween. The first cylindrical bore 158 is operable to receive a head 164 of the assembly bolt 126 and the second cylindrical bore 160 is operable to slidably receive a threaded shaft 166 of the assembly bolt 126.

The operation of assembling the work hardened modular component connector 120 will now be described. First, it should again be understood that the work hardened modular component connector 120 may be utilized with various modular orthopedic implants such as the modular knee prosthesis 106, as shown in FIG. 6, or any other prosthesis or device having modular components which require joining or coupling of the modular components. For example, here again, the male member 122 may form a part of a stem for a modular hip prosthesis, while the female member 124 may form the proximal portion of the modular hip prosthesis.

The male member 122 is first inserted into the female member 124 such that the first tapered portion 130 of the male member 122 congruently mates or engages the first frustoconical bore 146 defined by a tapered inner side wall 168. With the tapered portion 130 fully engaged within the bore 146, the external machined surface 136 frictionally locks with the inner side wall 168, as the first proximal end 138 is positioned adjacent to the terminal end 152 of the bore 146. The male member 122 may then be struck with an appropriate tool to fully seat the male member 122 within the female member 124.

Once fully seated, the transition corner 132 is positioned inbound from the entrance opening 150 at a stress concentration point or region 170. The cylindrical portion 134 then extends out of the entrance opening 150 having a diameter which is smaller than the entrance opening 150 diameter, as shown clearly in FIG. 7. The assembly bolt 126 is then slidably received through the second elongated bore 148 and threadably received within the threaded bore 144. With the threaded shaft 166 threadably engaging the threaded bore 144, the head 164 of the assembly bolt 126 comes to rest within the bore 158 upon the annular shoulder or ledge 162. The head 164 may be inserted using a hex driver or other appropriate driving mechanism. Alternatively, the assembly bolt 126 may also be eliminated since the male member 122 frictionally locks with the female member 124. With the transition corner 132 being mechanically or work hardened by cold working, the load or sheer strength of the male member 122 along the stress concentration point 170 is increased by at least 25% as compared to a non-work hardened male member 122.

Figures 8A, 8B:
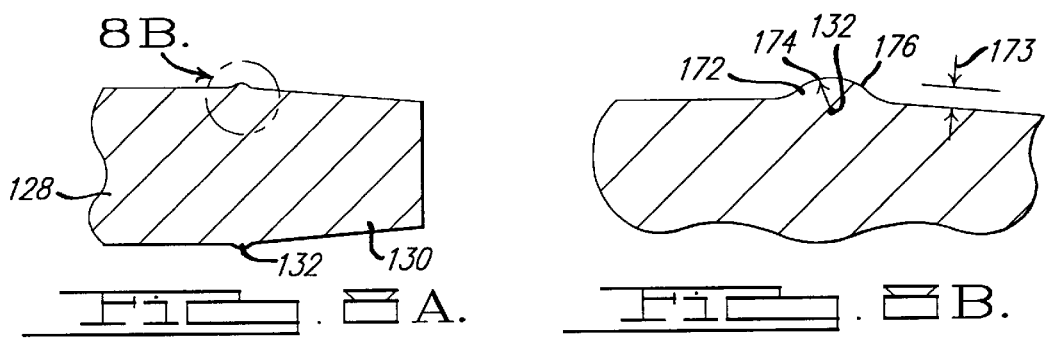
Figures 9A, 9B:
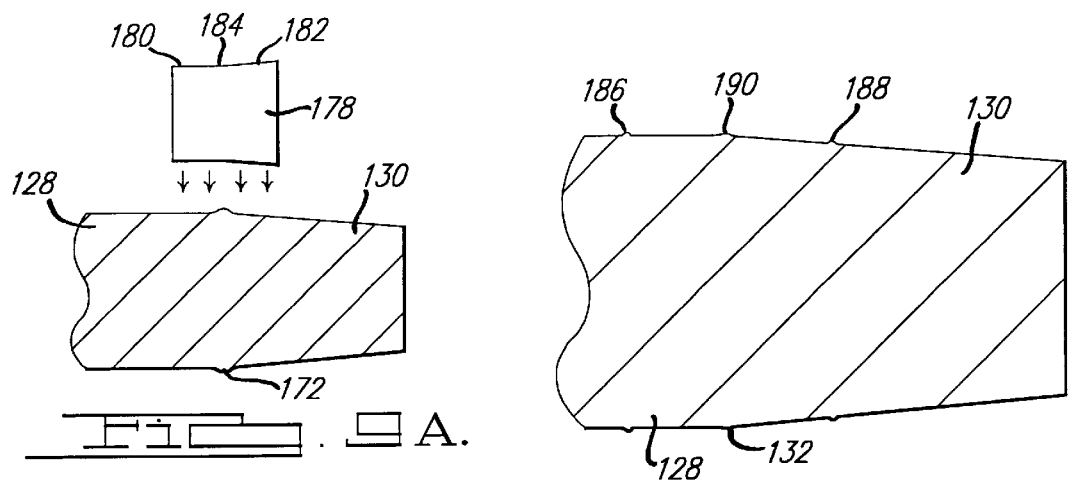
Figure 10:
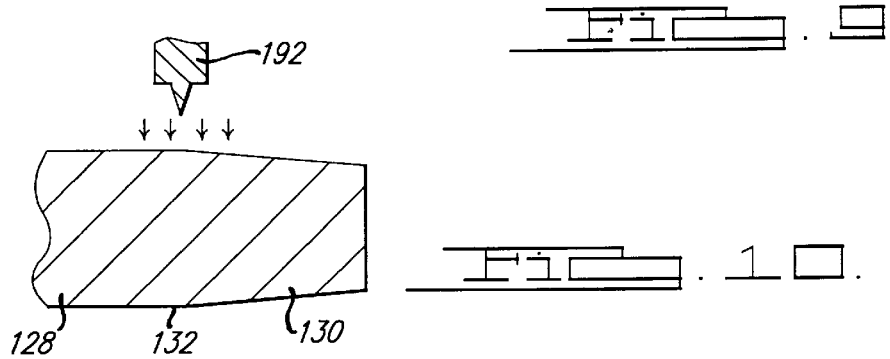

The method of forming the work hardened modular component connector 120 will now be described with reference to FIGS. 8–10. The female member 124 is first formed by machining or boring out the first frustoconical elongated bore 146 and the second elongated bore 148 using an appropriate tool such as a CNC boring machine. Once the female member 124 is formed, the first step in forming the male member 122 is to provide a cylindrical titanium piece of stock. This piece of stock is inserted into a conventional precision CNC lathe. Once positioned within the lathe, the first cylindrical portion 134 and the second tapered portion 136 are formed by machining or axially turning the cylindrical piece of stock and axially drawing a single point cutting member along this stock.

The tapered portion 136 is turned slightly oversized by about 0.006 inches along the entire length L of the tapered portion 136. In addition, a toroidal bulbous hump 172 is also formed at the transition corner 132. The bulbous hump 172 is centered at the transition corner 132 to have approximately 0.1 inches on either side of the center of the transition corner 132 providing for a thickness or height of the bulbous hump 172 of about 0.015 inches, identified by reference numeral 173 and a radius of about 0.32 inches, identified by reference numeral 174, shown clearly in FIG. 8B. The radius 174 thus yields the displaced thickness 173 of about 0.015 inches and an axial width of about 0.200 inches centered at the transition corner 132 to form a bulbous surface 176. It should be noted that the cylindrical portion 128 and the tapered portion 130 along with the bulbous external surface 176 are formed to an initial configuration during the same machining or turning process so that each portion is substantially concentric with one another.

Once the tapered region 130 is formed slightly oversized along with the bulbous hump 172, the bulbous hump 172 is work hardened by cold working. The cold working is performed by three (3) rollers 178 positioned in a chuck jaw circumferencially spaced about the male member 122. As shown in FIG. 9A, each roller 178 includes a cylindrical planer region 180 and angled or tapered region 182 each being substantially congruent with the male member 122 with a transition corner 184 positioned therebetween. The bulbous hump 172 is reduced in size by forcing the three (3) rollers 178 into the bulbous hump 172, while rotating the male member 122, the rollers 178 rotatably engage the male member 122.

The material forming the bulbous hump 172 is displaced into the transition corner 132, thereby work hardening the stress concentration region located at the transition corner 132. The cold working with the rollers 178 work hardens and shapes the bulbous area 172 to provide a sufficiently thick work hardened area, thereby increasing the load or sheer strength along this stress concentration point by at least 25% over a non-work hardened device. Here again, it should be understood that various other mechanical or work hardening techniques can also be performed in this area.

After the cold working is performed by the rollers 178, slight surface irregularities are created at each end of the rollers 178 which can distort the external cylindrical surfaces 134 and 136, as shown at points 186 and 188. In addition, the transition corner 132 may also have surface irregularities due to the extensive cold working in this area which forces the bulbous hump 172 into this region, identified by point 190. To provide a final precision configuration, the surface irregularities 186, 188 and 190 are machined or removed using a single point cutting member 192 on the CNC lathe. The cutting member 192 removes the surface irregularity 186, shapes the transition corner 132 by removing the surface irregularity 190, as well as removes the oversized material of about 0.006 inches along the entire length L of the tapered portion 130, thus removing the surface irregularity 188.

By only removing a very thin layer from the transition corner 132, the majority of the work hardened thickness is not removed, thereby increasing the strength in the corner 132 by at least 25%. It should further be noted that the bulbous hump 172 can be formed at any point where there is a stress concentration and work hardened in a similar manner as set forth above to increase the strength at the stress concentration region of the joint. Furthermore, the entire tapered portion 130 can be cold worked to provide enhanced strength along the entire tapered portion 130. However, this would require larger equipment and much higher forces to work harden this enlarged area. With the final precision configuration machined, the threaded internal bore 144 is finally formed within the male member 122.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention.

What is claimed is:

1. A method of forming a work hardened orthopedic joint having a male member and a female member for use in an orthopedic surgical procedure, said method comprising:

machining the male member by removing excess material to form a first cylindrical portion and a second tapered portion with an oversized region located therebetween at a stress concentration area of the male member where the oversized region on the male member extends beyond a final configuration of the male member;

reducing the size of the oversized region by cold rolling at least a portion of the oversized region into the male member to form a concentrated work hardened contact area at the stress concentration area of the male member;

machining the male member into the final configuration to remove any remaining portion of the oversized region that extends beyond the final configuration; and joining the male member with the female member, whereby at least a portion of the concentrated work hardened contact area at the stress concentration area of the male member engages the female member.

2. The method as defined in claim 1 wherein the step of machining the male member further includes machining a bulbous hump between the first cylindrical portion and the second tapered portion by axially turning the male member and drawing a cutting member along the male member.

3. The method as defined in claim 2 wherein the step of machining the male member into the final configuration further includes the step of removing any surface irregularities created by cold rolling the bulbous hump by turning the male member on a lathe.

4. The method as defined in claim 1 further comprising the step of machining a a bore into the female member that is operable to receive the male member.

5. The method as defined in claim 1 further comprising implanting the orthopedic joint having the male member and the female member during the orthopedic surgical procedure.

6. The method as defined in claim 1 wherein the step of machining the first cylindrical portion and the second tapered portion with the oversized region therebetween is machined as a single process, whereby the first cylindrical portion, the second tapered portion and the oversized region are all concentric with one another.

7. The method as defined in claim 1 wherein the orthopedic joint is made from a suitable biocompatible material selected from a group consisting of titanium, stainless steel, titanium alloy and cobalt-chrome-molybdenum alloy.

8. The method as defined in claim 1 further comprising machining the oversized region to have a thickness of about 0.015 inches.

9. The method as defined in claim 1 wherein machining the male member by removing excess material further comprises machining the second tapered portion oversized.

10. A method of forming a work hardened orthopedic joint having a male member and a female member for use in an orthopedic surgical procedure, said method comprising:

machining a first cylindrical portion and a second tapered portion with a bulbous hump therebetween into the male member at a stress concentration area of the male member by axially turning the male member and drawing a cutting member along the male member whereby the bulbous hump on the male member extends beyond a final configuration of the male member;

reducing the size of the bulbous hump by cold rolling the bulbous hump into a transition corner on the male member to form a concentrated work hardened contact area at the stress concentration area of the male member;

machining the male member into the final configuration to remove any remaining portion of the oversized region that extends beyond the final configuration;

machining a first bore in the female member; and joining the male member within the female, whereby at least a portion of the concentrated work hardened contact area at the stress concentration area of the male member engages the bore of the female member.

11. The method as defined in claim 10 further comprising the steps of machining a second bore in the female member and machining a threaded bore at a first end of the male member, wherein said threaded bore in the male member and the second bore in the female member are operable to receive an assembly bolt.

12. The method as defined in claim 10 further comprising implanting the orthopedic joint having the male member and the female member during the orthopedic surgical procedure.

13. The method as defined in claim 10 wherein the orthopedic joint is made from a suitable biocompatible material selected from a group consisting of titanium, stainless steel, titanium alloy and cobalt-chrome-molybdenum alloy.

14. The method as defined in claim 10 further comprising machining the bulbous hump to have a thickness of about 0.015 inches.

15. The method as defined in claim 10 wherein machining the male member by axially turning the male member and drawing a cutting member along the male member further comprises machining the second tapered portion oversized.

16. A method of forming a work hardened orthopedic joint having a male member and a female member for use in an orthopedic surgical procedure, said method comprising:

turning the male member on a lathe to form an oversized region on the male member by drawing a cutting member along the male member where the oversized region extends beyond a final configuration of the male member;

cold rolling at least a portion of the oversized region into the male member to form a concentrated work hardened contact area on the male member;

turning the male member on a lathe and forming a final configuration to remove any remaining portion of the oversized region that extends beyond the final configuration by drawing a cutting member along the male member; and joining the male member with the female member, whereby at least a portion of the concentrated work hardened contact area of the male member engages the female member.

17. The method as defined in claim 16 further comprising turning the male member on the lathe to form a first cylindrical portion and a second tapered portion with the oversized region located therebetween by drawing the cutting member along the male member.

18. The method as defined in claim 16 further comprising the step of implanting the orthopedic joint having the first member and the second member during the orthopedic surgical procedure.

19. The method as defined in claim 16 wherein the orthopedic joint is made from a suitable biocompatible material selected from a group consisting of titanium, stainless steel, titanium alloy and cobalt-chrome-molybdenum alloy.

20. The method as defined in claim 16 further comprising forming the oversized region to have a thickness of about 0.015 inches.

* * * * *

UNITED STATES PATENT AND TRADEMARK OFFICE
CERTIFICATE OF CORRECTION

PATENT NO.    : 6,067,701
DATED         : May 30, 2000
INVENTOR(S)   : Mark V. Vandewalle Page 1 of 1

It is certified that error appears in the above-identified patent and that said Letters Patent is hereby corrected as shown below:

Column 1,
Line 58, after "one" insert -- of --.

Column 3,
Line 60, "alloys etc." should be -- alloys, etc. --.

Column 5,
Line 23, "slidewall" should be -- sidewall --.
Line 25, "slidewall" should be -- sidewall --.

Column 6,
Line 59, "surface" should be -- surfaced --.

Column 7,
Line 55, "alloys etc." should be -- alloys, etc. --.
Line 59, "there between" should be -- therebetween --.

Column 8,
Line 13, "there through" should be -- therethrough --.

Column 10,
Line 62, delete 2nd occurrence of "a".

Signed and Sealed this

Thirtieth Day of April, 2002

Attest:

Attesting Officer

JAMES E. ROGAN
Director of the United States Patent and Trademark Office